United States Patent
Wirch et al.

(10) Patent No.: US 10,943,346 B2
(45) Date of Patent: Mar. 9, 2021

(54) MULTI-SAMPLE WHOLE SLIDE IMAGE PROCESSING IN DIGITAL PATHOLOGY VIA MULTI-RESOLUTION REGISTRATION AND MACHINE LEARNING

(71) Applicant: Corista, LLC, Concord, MA (US)

(72) Inventors: Eric W. Wirch, Somerville, MA (US); Alexander Andryushkin, Ayer, MA (US); Richard Y. Wingard, II, Newton, MA (US); Nigel Lee, Chestnut Hill, MA (US); Aristana Olivia Scourtas, Nahant, MA (US); David C. Wilbur, Pelham, NH (US)

(73) Assignee: CORISTA, LLC, Concord, MA (US)

(*) Notice: Subject to any disclaimer, the term of this patent is extended or adjusted under 35 U.S.C. 154(b) by 17 days.

(21) Appl. No.: 16/393,876

(22) Filed: Apr. 24, 2019

(65) Prior Publication Data
US 2019/0355113 A1    Nov. 21, 2019

Related U.S. Application Data

(60) Provisional application No. 62/674,368, filed on May 21, 2018.

(51) Int. Cl.
*G06T 7/00* (2017.01)
*G06K 9/00* (2006.01)
(Continued)

(52) U.S. Cl.
CPC .......... *G06T 7/0012* (2013.01); *G06F 3/0485* (2013.01); *G06F 3/04845* (2013.01);
(Continued)

(58) Field of Classification Search
CPC ... G06T 7/0012; G06T 3/0075; G06T 3/4053; G06T 7/194; G06T 2207/30024;
(Continued)

(56) References Cited

U.S. PATENT DOCUMENTS

| 5,561,556 A | 10/1996 | Weissman |
| 5,733,721 A | 3/1998 | Hemstreet, III et al. |

(Continued)

FOREIGN PATENT DOCUMENTS

| WO | WO 2017/087415 A1 | 5/2017 |
| WO | 2018/129318 A2 | 7/2018 |
| WO | 2019/226270 | 11/2019 |

OTHER PUBLICATIONS

International Search Report and Written Opinion for In'l Application No. PCT/US2019/029006, titled: Multi-sample Whole Slide Image Processing via Multi-resolution Registration, dated Sep. 16, 2019.

(Continued)

*Primary Examiner* — Xuemei G Chen
(74) *Attorney, Agent, or Firm* — Hamilton, Brook, Smith & Reynolds, P.C.

(57) ABSTRACT

When reviewing digital pathology tissue specimens, multiple slides may be created from thin, sequential slices of tissue. These slices may then be prepared with various stains and digitized to generate a Whole Slide Image (WSI). Review of multiple WSIs is challenging because of the lack of homogeneity across the images. In embodiments, to facilitate review, WSIs are aligned with a multi-resolution registration algorithm, normalized for improved processing, annotated by an expert user, and divided into image patches. The image patches may be used to train a Machine Learning model to identify features useful for detection and classification of regions of interest (ROIs) in images. The trained model may be applied to other images to detect and classify ROIs in the other images, which can aid in navigating the WSIs. When the resulting ROIs are presented to the user, the user may easily navigate and provide feedback through a display layer.

16 Claims, 11 Drawing Sheets

(51) Int. Cl.
  *G06K 9/62* (2006.01)
  *G06T 3/00* (2006.01)
  *G06F 3/0485* (2013.01)
  *G06F 3/0484* (2013.01)
  *G06T 3/40* (2006.01)
  *G06T 7/194* (2017.01)

(52) U.S. Cl.
  CPC ....... *G06K 9/0014* (2013.01); *G06K 9/00147* (2013.01); *G06K 9/628* (2013.01); *G06K 9/6253* (2013.01); *G06K 9/6257* (2013.01); *G06K 9/6262* (2013.01); *G06T 3/0075* (2013.01); *G06T 3/4053* (2013.01); *G06T 7/194* (2017.01); *G06F 2203/04806* (2013.01); *G06T 2200/24* (2013.01); *G06T 2207/20016* (2013.01); *G06T 2207/20081* (2013.01); *G06T 2207/20084* (2013.01); *G06T 2207/20092* (2013.01); *G06T 2207/30024* (2013.01)

(58) Field of Classification Search
  CPC . G06T 2207/20081; G06T 2207/20016; G06T 2200/24; G06T 2207/20092; G06T 2207/20084; G06T 2207/10024; G06T 2207/10056; G06T 2207/20021; G06T 7/33; G06T 7/136; G06T 7/11; G06K 9/00147; G06K 9/0014; G06K 9/628; G06K 9/6257; G06K 9/6262; G06K 9/6253; G06K 9/4642; G06K 9/6267; G06K 9/6254; G06F 3/0485; G06F 3/04845; G06F 2203/04806; G06F 3/0484
  See application file for complete search history.

(56) References Cited

U.S. PATENT DOCUMENTS

| | | | |
|---|---|---|---|
| 5,741,648 A | 4/1998 | Hemstreet, III et al. | |
| 5,956,418 A * | 9/1999 | Aiger | G06T 3/4038 |
| | | | 382/154 |
| 6,011,809 A | 1/2000 | Tosaka | |
| 6,049,421 A | 4/2000 | Raz et al. | |
| 6,466,352 B1 | 10/2002 | Shahar et al. | |
| 6,606,413 B1 | 8/2003 | Zeineh | |
| 6,650,357 B1 | 11/2003 | Richardson | |
| 6,798,571 B2 | 9/2004 | Wetzel et al. | |
| 6,905,300 B1 | 6/2005 | Russum | |
| 6,961,080 B2 | 11/2005 | Richardson | |
| 7,109,464 B2 | 9/2006 | Cartlidge et al. | |
| 7,132,636 B1 | 11/2006 | Cartlidge et al. | |
| 7,151,246 B2 | 12/2006 | Fein et al. | |
| 7,155,049 B2 | 12/2006 | Wetzel et al. | |
| 7,224,839 B2 | 5/2007 | Zeineh | |
| 7,248,716 B2 | 7/2007 | Fein et al. | |
| 7,338,168 B2 | 3/2008 | Cartlidge et al. | |
| 7,346,200 B1 | 3/2008 | Tsipouras et al. | |
| 7,417,213 B2 | 8/2008 | Krief et al. | |
| 7,463,761 B2 | 12/2008 | Eichhorn et al. | |
| 7,518,652 B2 | 4/2009 | Olson et al. | |
| 7,522,757 B2 | 4/2009 | Tsipouras et al. | |
| 7,605,356 B2 | 10/2009 | Krief et al. | |
| 7,638,748 B2 | 12/2009 | Krief et al. | |
| 7,640,112 B2 | 12/2009 | Tsipouras et al. | |
| 7,646,495 B2 | 1/2010 | Olsen et al. | |
| 7,689,024 B2 | 3/2010 | Eichhorn et al. | |
| 7,692,131 B2 | 4/2010 | Fein et al. | |
| 7,756,357 B2 | 7/2010 | Yoneyama | |
| 7,772,535 B2 | 8/2010 | Krief et al. | |
| 7,835,869 B2 | 11/2010 | Tsipouras et al. | |
| 7,863,552 B2 | 1/2011 | Cartlidge et al. | |
| 7,867,126 B2 | 1/2011 | Nakajima et al. | |
| 7,876,948 B2 | 1/2011 | Wetzel et al. | |
| 7,901,887 B2 | 3/2011 | Tafas et al. | |
| 7,945,391 B2 | 5/2011 | Tsipouras et al. | |
| 8,170,698 B1 | 5/2012 | Gusack | |
| 8,271,251 B2 | 9/2012 | Schwartz et al. | |
| 8,574,590 B2 | 11/2013 | Doranz et al. | |
| 8,774,518 B2 | 7/2014 | Cosatto et al. | |
| 8,879,813 B1 * | 11/2014 | Solanki | G06T 3/0093 |
| | | | 382/128 |
| 8,891,851 B2 | 11/2014 | Spaulding | |
| 8,896,620 B2 | 11/2014 | Orrock | |
| 8,897,537 B2 | 11/2014 | Cosatto et al. | |
| 8,934,699 B2 | 1/2015 | Yamane et al. | |
| 8,934,718 B2 | 1/2015 | Cosatto et al. | |
| 9,036,255 B2 | 5/2015 | Loncy et al. | |
| 9,097,909 B2 | 8/2015 | Halushka | |
| 9,134,524 B2 | 9/2015 | Yamamoto et al. | |
| 9,213,027 B2 | 12/2015 | Doranz et al. | |
| 9,217,694 B2 | 12/2015 | Sieckmann et al. | |
| 9,224,106 B2 | 12/2015 | Cosatto et al. | |
| 9,332,190 B2 | 5/2016 | Murakami | |
| 9,335,534 B2 | 5/2016 | Schaudraff | |
| 9,430,829 B2 * | 8/2016 | Madabhushi | G06T 7/0012 |
| 9,547,898 B2 | 1/2017 | Hall et al. | |
| 9,575,301 B2 | 2/2017 | Loney et al. | |
| 9,581,800 B2 | 2/2017 | Corwin et al. | |
| 9,609,196 B2 | 3/2017 | Yamakawa et al. | |
| 9,712,732 B2 | 7/2017 | Kancko et al. | |
| 9,759,551 B2 | 9/2017 | Schaudraff et al. | |
| 9,772,282 B2 | 9/2017 | Tucker-Schwartz et al. | |
| 9,791,659 B2 | 10/2017 | Yamakawa et al. | |
| 9,805,166 B1 | 10/2017 | Spaulding | |
| 9,818,190 B2 | 11/2017 | Chukka et al. | |
| 9,846,938 B2 | 12/2017 | Steigauf et al. | |
| 9,892,341 B2 | 2/2018 | Reicher et al. | |
| 9,928,278 B2 | 3/2018 | Welinder et al. | |
| 9,934,568 B2 | 4/2018 | Reicher et al. | |
| 9,940,719 B2 | 4/2018 | Kneepkens | |
| 9,963,745 B2 | 5/2018 | Mai et al. | |
| 9,972,087 B2 | 5/2018 | Isoda et al. | |
| 9,979,868 B2 | 5/2018 | Fujinami et al. | |
| 10,012,537 B2 | 7/2018 | Garsha et al. | |
| 10,048,462 B2 | 8/2018 | Mitsuyasu | |
| 10,049,450 B2 * | 8/2018 | Madabhushi | G06N 3/08 |
| 10,061,107 B2 | 8/2018 | Loney et al. | |
| 10,102,418 B2 * | 10/2018 | Bredno | G06K 9/66 |
| 10,175,154 B2 | 1/2019 | Campbell | |
| 10,444,486 B2 | 10/2019 | Rainbolt et al. | |
| 10,489,633 B2 * | 11/2019 | Molin | G06K 9/2081 |
| 10,527,836 B2 | 1/2020 | Sakamoto et al. | |
| 10,572,725 B1 * | 2/2020 | Becker | G06K 9/00442 |
| 10,573,001 B2 | 2/2020 | Bredno et al. | |
| 10,600,184 B2 * | 3/2020 | Golden | G06N 3/084 |
| 10,643,396 B2 * | 5/2020 | Eastwood | G06T 15/08 |
| 10,663,711 B2 | 5/2020 | Wirch et al. | |
| 2008/0123916 A1 | 5/2008 | Adams et al. | |
| 2010/0194681 A1 | 8/2010 | Halushka | |
| 2011/0158491 A1 * | 6/2011 | Markova | G06T 7/41 |
| | | | 382/128 |
| 2012/0002034 A1 | 1/2012 | Matsunobu et al. | |
| 2012/0068928 A1 | 3/2012 | Bruss et al. | |
| 2013/0077891 A1 * | 3/2013 | Nimnual | G06T 7/37 |
| | | | 382/276 |
| 2013/0339260 A1 * | 12/2013 | Johnson | G06Q 30/0185 |
| | | | 705/318 |
| 2014/0257857 A1 | 9/2014 | Meissner et al. | |
| 2015/0110348 A1 | 4/2015 | Solanki et al. | |
| 2015/0279032 A1 | 10/2015 | Hall et al. | |
| 2015/0330776 A1 | 11/2015 | Hayashi et al. | |
| 2016/0019691 A1 * | 1/2016 | Imamura | G06T 5/50 |
| | | | 382/128 |
| 2016/0019695 A1 | 1/2016 | Chukka et al. | |
| 2016/0042511 A1 | 2/2016 | Chukka et al. | |
| 2016/0157751 A1 * | 6/2016 | Mahfouz | A61B 5/062 |
| | | | 600/409 |
| 2016/0252713 A1 | 9/2016 | Corwin | |
| 2016/0321809 A1 | 11/2016 | Chukka et al. | |
| 2016/0350651 A1 * | 12/2016 | Devarajan | G06F 40/20 |
| 2017/0169567 A1 * | 6/2017 | Chefd'hotel | G06K 9/00127 |
| 2017/0185846 A1 * | 6/2017 | Hwangbo | G06K 9/628 |
| 2017/0348509 A1 | 12/2017 | Burkholz et al. | |
| 2017/0372471 A1 | 12/2017 | Euren | |

(56) References Cited

U.S. PATENT DOCUMENTS

| | | | |
|---|---|---|---|
| 2018/0188519 A1 | 7/2018 | Wirch et al. | |
| 2018/0247408 A1* | 8/2018 | Wang | G06K 9/6202 |
| 2018/0315193 A1* | 11/2018 | Paschalakis | G06K 9/00617 |
| 2018/0322632 A1* | 11/2018 | Barnes | G06T 7/11 |
| 2018/0374210 A1* | 12/2018 | Barker | G06T 7/0012 |
| 2019/0164054 A1* | 5/2019 | Lee | G06N 3/0454 |
| 2019/0293637 A1* | 9/2019 | Day | G01N 33/5306 |
| 2019/0304092 A1* | 10/2019 | Akselrod-Ballin | G06T 7/143 |
| 2019/0362841 A1* | 11/2019 | Aysin | G06N 3/04 |
| 2020/0126207 A1* | 4/2020 | Saltz | G06T 7/0012 |
| 2020/0167930 A1* | 5/2020 | Wang | G06T 7/0012 |
| 2020/0211191 A1* | 7/2020 | Joshi | G06K 9/00604 |
| 2020/0348503 A1 | 11/2020 | Wirch et al. | |

OTHER PUBLICATIONS

Trahearn, Nicholas et al., "Hyper-Stain Inspector: A Framework for Robust Registration and Localised Co-Expression Analysis of Multiple Whole-Slide Images of Serial Histology Sections," *Scientific Reports*, 7: 5641, 13 pages (Published Jul. 2017).

Roullier, Vincent et al., "Multi-resolution graph-based analysis of histopathological whole slide images: Application to mitotic cell extraction and visualization," *Computerized Medical Imaging and Graphics*, 35: 603-615 (2011).

Rojo, M.G., et al., "Critical Comparison of 31 Commercially Available Digital Slide Systems in Pathology," International Journal of Surgical Pathology, vol. 14, No. 4, pp. 285-305, Oct. 1, 2006.

\* cited by examiner

Figure 1: System Workflow Overview

Figure 2: Preprocessing

Figure 3: Registration

Figure 4: CNN Training

Figure 5: CNN Validation

Figure 6: CNN Evaluation

Figure 9: User Interface

MULTI-SAMPLE WHOLE SLIDE IMAGE PROCESSING IN DIGITAL PATHOLOGY VIA MULTI-RESOLUTION REGISTRATION AND MACHINE LEARNING

RELATED APPLICATION(S)

This application claims the benefit of U.S. Provisional Application No. 62/674,368, filed on May 21, 2018. The entire teachings of the above application(s) are incorporated herein by reference.

BACKGROUND

When reviewing digital pathology tissue specimens, multiple slides may be created from thin, sequential slices of tissue. These slices may then be prepared with various stains and digitized to generate a Whole Slide Image (WSI). Review of multiple WSIs is challenging because of the lack of homogeneity across the images.

SUMMARY

In embodiments, to facilitate review, WSIs are aligned with a multi-resolution registration algorithm, normalized for improved processing, annotated by an expert user, and divided into image patches. The image patches may be used to train a Machine Learning (ML) algorithm to identify features useful for detection and classification of Regions of Interest (ROIs) in images. The trained ML model may be applied to other images to detect and classify ROIs in the other images, which can aid in navigating the WSIs. When the resulting ROIs are presented to the user, the user may easily navigate and provide feedback through a display layer.

In one example embodiment, a system is provided for analyzing WSIs of tissue specimens. The system may include a computer processing system having at least one processor communicatively coupled to memory that is configured to analyze WSI of the tissue specimens.

For WSI in a set of slides with a plurality of stains, a stain type for a WSI may be specified by the system. The stain type may be specified by the system through one of: metadata from another system, manual labeling by a pathologist or other domain expert, or an automatic stain detector. The WSI may be preprocessed to form an intermediate form of the data, which separates the foreground tissue from the background and normalizes the WSI data based on parameters of a ML model, where the parameters include the possible stains as well as resolution or other parameters.

The WSI may be presented for annotation, where the annotation may involve applying non-default classification labels to regions of the WSI data via a user interface by a pathologist or other domain expert. Image patches may be created from the annotated regions, each image patch corresponding to a single class. The parameter appropriate ML model that dynamically generates features useful for classification may be trained. The trained ML model classifier may be applied to unannotated WSI data to produce a set of classifications for the stain and patch parameters.

The preprocessed WSIs from the stain sets may be registered via a multi-resolution registration algorithm. The multi-resolution registration algorithm may include (1) an application of a coarse registration algorithm to produce a general Affine Transform Matrix and (2) iterative registration on successively smaller subsections to produce a sparse hierarchical multi-resolution ATM pyramid, which is then processed to generate a non-sparse Field of Affine Transform Matrices (fATMs) such that corresponding regions between images are aligned to the highest degree possible based on tissue and imaging variations.

The produced set of non-default classifications from multiple stain sets may be aggregated, such that each set of classifications may be generated by applying a stain-specific, trained ML model to the normalized WSI data, with the aggregation achieved through the translation of the non-default classifications using the fATMs generated for the individual WSIs;

The aggregated non-default classifications from each of the multiple WSIs in the stain set may be correlated. The individual classifications may be correlated by enhancing true classifications and removing false classifications, resulting in one or more non-default classified regions for a given stain set and metadata for the one or more non-default classified regions of the given stain set.

In an example embodiment, a system may be provided for presenting a stain set of registered WSIs and annotations. The computer processing system may include at least one processor communicatively coupled to memory. The processor may be configured to present each image of the stain set in a separate viewing panel of a plurality of viewing panels. The processor may be configured to display a set of annotated regions of an image and corresponding metadata in an organized tabular display, along with the plurality of viewing panels. The processor may be configured to enable capability for a user to: (i) click on one of the set of annotated regions in the organized tabular display and (ii) navigate all of the plurality of viewing panels to the same location by making use of previously calculated registration information of the images. The processor may be configured to enable capability for a user to: (i) apply navigation events within one or more of the plurality of viewing panels, including dragging, zooming, and panning, and (ii) subsequently move all of the registered viewing panels to the same location by making use of the previously calculated registration information of the image;

The processor may be configured to enable capability for a user to disable navigation of the plurality of viewing panels to the same location. The processor may be configured to enable capability for a user to provide additional annotated regions, at least one of the additional annotated regions corresponding to labeling of image regions improperly annotated, including missed annotations or misclassified annotations.

BRIEF DESCRIPTION OF THE DRAWINGS

The foregoing will be apparent from the following more particular description of example embodiments, as illustrated in the accompanying drawings in which like-reference characters refer to the same parts throughout the different views. The drawings are not necessarily to scale, emphasis instead being placed upon illustrating embodiments.

DETAILED DESCRIPTION

Figure 1:
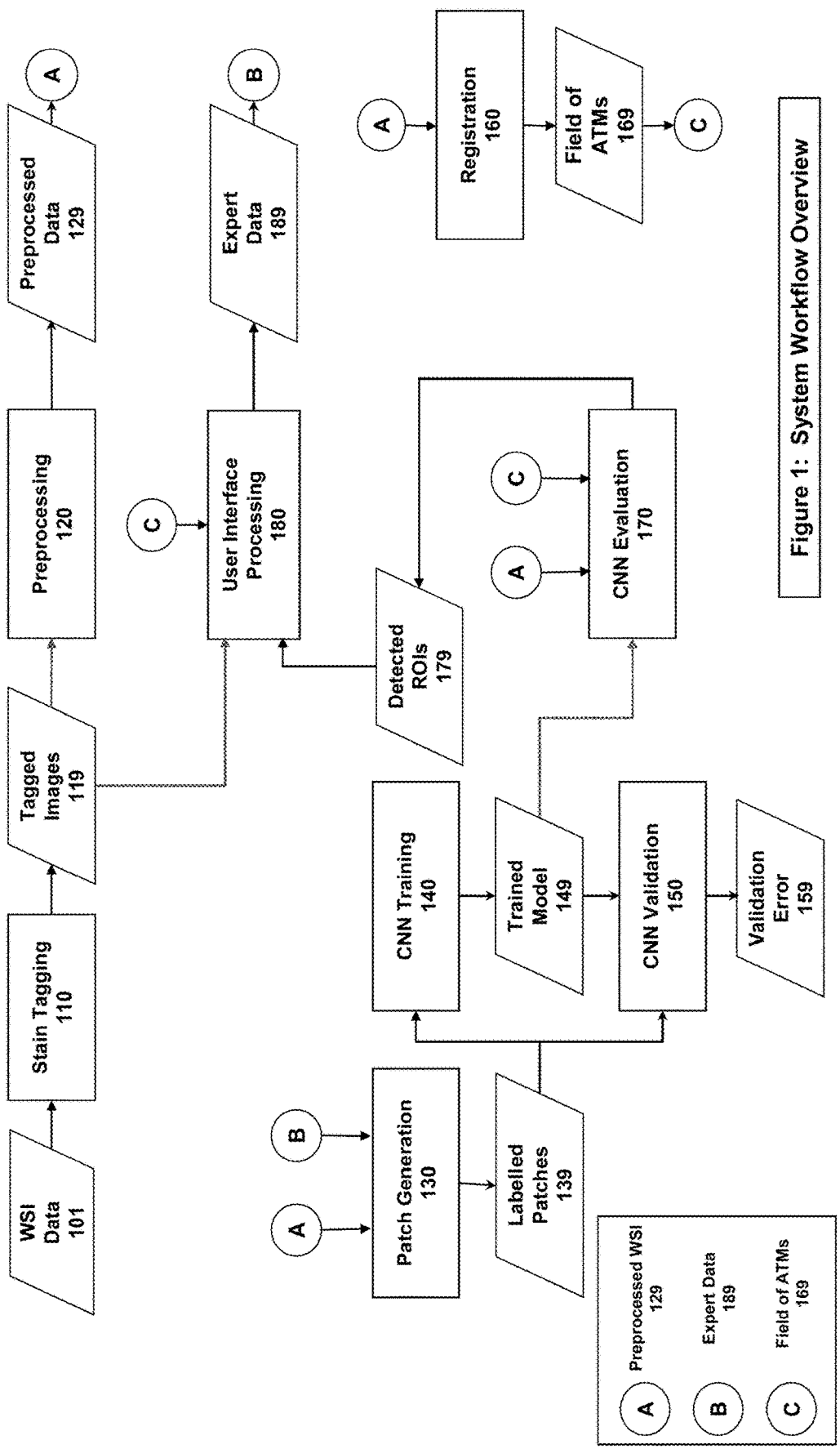
FIG. 1 illustrates an example system/method implementation in embodiments of the present invention.

A description of example embodiments follows.

The teachings of all patents, published applications and references cited herein are incorporated by reference in their entirety.

For many medical imaging applications, but especially in the field of pathology, current state of the art requires the viewing of multiple data samples for a particular specimen. The data samples may be viewed in either the analog or digital domain. The samples to be viewed are created by producing multiple glass slides from a single specimen. These slides are thin, sequential slices of tissue from the single specimen. As the slices are typically generated sequentially, the morphology and structures contained within a series of slides are similar but not identical; the pieces of tissue and the structures within each slide are irregular objects, like a cross-section of a tree trunk, and the structures and the overall tissue shape change from one slide to the next. The slices are then prepared using different stains that allow for better viewing of various types of structures within the tissue.

To view the samples in the analog domain, the pathologist views the slides using different light sources and filters (visible light, fluorescent, polarization, and such) under a microscope in order to provide a review.

To view the samples in the digital domain, the pathologist views the slides using either a microscope-mounted camera or using a Whole Slide Imaging device (digitizer) to produce a Whole Slide Image (WSI). In both instances, the captured images are displayed on a computer monitor.

In both the analog and digital domain, the current state of the art requires the pathologist to view each sample (slide or WSI) in a serial manner. When the pathologist sees a region of interest on one slide or image, the pathologist must manually locate the corresponding region on other slides to see the corresponding information. By extension, the use of digital Whole Slide Images (WSIs) for tasks beyond viewing by a human, such as when applying Machine Learning (ML) or utilizing Computer Vision (CV) algorithms, is challenging because of the irregularities and lack of direct correlation between images of different slides.

Embodiments of the present invention herein describe a workflow (method or process) for effectively reviewing specimens in digital pathology. Additionally, the present invention provides additional utility, for both the current WSIs and similar future WSIs, by allowing data to be used for training models, or for inferencing the current WSIs against a trained model, to assist in pre-screening, case review or quality reviews, utilizing more information from the WSI than is currently available or utilized in the analog domain. In the workflow, a set of images for a specimen containing progressively different structures (based on both sample variation and on the stains and light sources) may be preprocessed (color and resolution normalized), evaluated for desired features, aligned (registered) across stains, post-processed (correlated), and displayed to a user. Preprocessing may include color normalization to account for stain variations from different organizations, scanners, and technicians. Evaluation (also referred to as inferencing) may be carried out via one or more machine learning (ML) algorithms. Cross-stain image alignment may be accomplished via a multi-resolution registration algorithm. Post-processing may include boosting of strong detections and removal of weak ones using ML outputs from multiple stain sections, to produce a cleaner, more sensible display to the user. Additional embodiments describe the process by which an expert can create the ground truth for training an ML algorithm. Additionally, the expert may provide feedback on the results from an initial evaluation in order to retrain or augment an ML algorithm to improve accuracy.

Embodiments of the Machine Learning algorithms which are implemented within the embodiment of the current invention include Deep Learning or Convolutional Neural Networks (CNNs), Region-based CNNs (R-CNN), Support Vector Machines (SVMs), AutoEncoders (AEs) or Shallow Neural Networks (SNNs).

System Implementation

FIG. 1 shows one example system/method implementation in embodiments of the present invention. At least two whole slide images (WSIs or WSI data) (101) are input into the system.

In the Stain Tagging stage (110), the system/method associates metadata containing the stain type with each WSI. This process can be done via user input, via externally supplied metadata or using an Automatic Stain Detection algorithm to determine the stain types of the WSI data. All 3 methods result in tagging (i.e., labelling) the WSI data with the identified stain types, producing Tagged Images (119). The system/method inputs the Tagged Images to both the User Interface Processing stage (180) for use by an expert user, and the Preprocessing Stage (120).

The Preprocessing stage (120 in FIGS. 1 & 2) is implemented by the system/method in the form of Background Removal (123), Color Normalization (125), and Resolution Normalization (127) to account for variations in stains, techniques, procedures, and WSI capture devices across different organizations. The output of the Preprocessing Stage is Preprocessed Data (129). The system/method inputs the Preprocessed Data (129) to the Registration stage (160) and to either the Patch Generation stage (130) or the Evaluation stage (170), depending on the intended use of the data (training & validation vs evaluation, respectively).

The Registration stage (160 in FIGS. 1 & 3) is implemented by the system/method in the form of taking two Preprocessed Data (129) inputs, first performing Coarse Alignment (162) using subsampled image data, generating keypoints or intensities which are analyzed to produce a Coarse ATM (163). Portions of the Preprocessed Data are recursively further processed using the Coarse ATM as an input in the Recursive Finer Alignment stage (164) to produce progressively finer Fine sub-ATMs (165). The system then combines the Coarse ATM (163) and the set of Fine sub-ATMs (165) to generate a single Field of ATMs (169)

during the fATM Composition stage (168). The generated Field of ATMs is then used in both the Evaluation stage (170) and User Interface Processing stage (180).

The Patch Generation stage (130 in FIGS. 1, 4 & 5), the system/method combines the Preprocessed Data (129) and the Expert Data (189) to generate Labeled Patches (139). The system/method then splits the set of Labeled Patches into Labeled Training Data (142) and Labeled Validation Data (152).

The Labeled Training Data (142) is used by the system/method in the CNN Training stage (140 of FIGS. 1 & 4) in the Train CNN stage (144). The result of the Train CNN stage is a CNN Model (149), which is used in both the CNN Validation stage (150) and Evaluation stage (170).

The Labeled Validation Data (152) is used by the system/method in the CNN Validation stage (150 of FIGS. 1 & 5) in the Classification stage (172) using a CNN Model (149). The Classification stage produces Classification Results (173), which are then compared to the correct classifications in the Labeled Validation Data (152) in the Validation stage (153). This produces a Validation Error (159) which is representative of the effectiveness of the CNN Model (149).

The system/method performs the Evaluation stage (170 of FIGS. 1 & 6) on Preprocessed Data (129) that has not been reviewed by an expert user. First it performs Classification (172) using a Trained Model (149) on the Preprocessed Data, producing Classification Results (173). The Classification Results may indicate either that the phenomenon of interest is absent (termed a "default" classification) or that the phenomenon of interest is present (termed a "non-default" classification). These Classification Results are combined with other Classification Results from the same stain set in the Cross-stain Correlation stage (174), to boost strong detections and filter weak ones based on locality within the image, which is determined through the use of Field of ATMs (169). The result of the Cross-stain Correlation is a set of Detected ROIs (179), which are then used in the User Interface Processing stage (180).

The User Interface Processing stage (180 on FIGS. 1 & 7), the system/method displays the Tagged Images (119) through the User Interface (UI) (182), and is ready to receive user input (185) through the User Interface (182) in the form of Annotations (187) that indicate the presence or absence of a phenomenon of interest, as well as (in some embodiments) the type of phenomenon. The navigation of multiple Tagged Images in the UI is facilitated through the use of Field of ATMs (169), which allow for the automatic co-navigation of images based on the user movements on a single image. The collection of annotations becomes the Expert Input (189) to the rest of the system.

Additionally, the User Interface Processing stage (180 on FIGS. 1 & 7) can display Detected ROIs (179), and can allow for the synchronized navigation between a user selected ROI on all images using the Field of ATMs (169). This allows for further expert annotation as described in FIG. 8.

Figure 8:
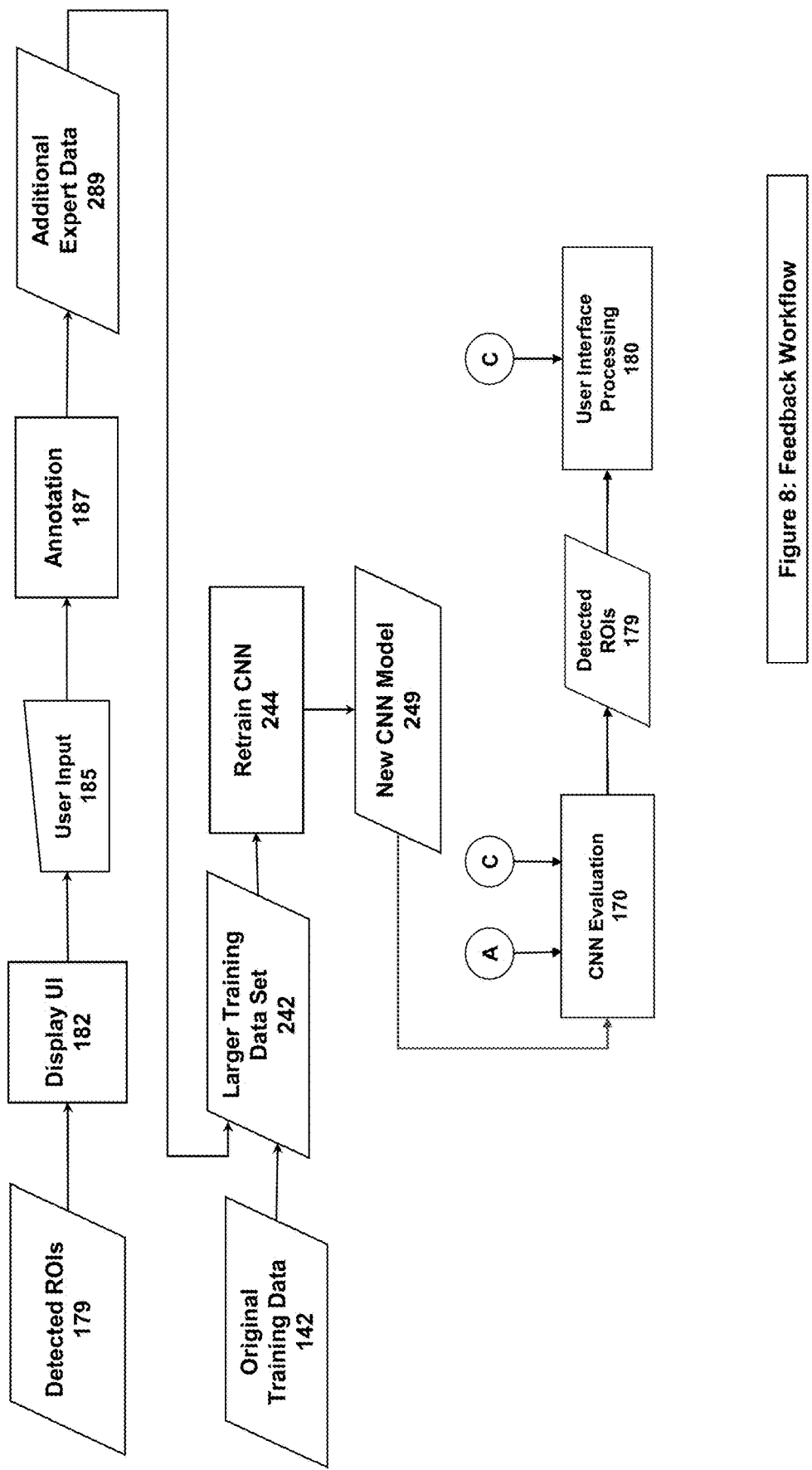
FIG. 8 illustrates an example system/method implementation of feedback processing with incremental training of the CNN in embodiments of the present invention.

FIG. 8 shows one example system/method implementation of feedback processing with incremental training of the CNN in embodiments of the present invention. In FIG. 8, the system/method displays Detected ROIs (179 from FIG. 1) in the Display UI (182). User Input (185) may take the form of additional Annotations (187) that mark image patches that have been incorrectly classified, producing Additional Expert Data (289). The system/method may combine this Additional Expert Data (289), consisting of the image patches with corrected annotations, with the Original Training Data (142) to form a Larger Training Data Set (242). The system/method may then Retrain (244) the CNN to form a New CNN Model (249). The system/method may then apply the New CNN Model to the Preprocessed Data (129) in a CNN Evaluation stage (170), taking additional new or existing Classification Results and correlating them using the Field of ATMs (169). The output is a new set of detected ROIs (179) that may again be displayed during the User Interface Processing stage (180).

Stain Tagging

Embodiments of the present invention perform stain detection on WSI data, such as in Stage 110 of FIG. 1. Physical tissue slices can be stained with different coloring agents, making different structural elements of the tissue, such as nuclei, membranes, etc., visible as distinctively colored areas. A majority of the widely used stains (e.g., H&E, trichrome, PAS, Basement Membrane, and such) are composed of several staining agents, thus yielding WSIs with specific color palettes. However, even for the same stain type, the WSI of the tissue might differ significantly between or within laboratories depending on the staining process details and staining chemicals used. Knowing the staining type of a particular WSI is important because some classification algorithms are stain-specific, since the stains emphasize different structures and features in the tissue.

In some embodiments, the stain type is specified by either externally supplied metadata or is assessed by an expert.

In another embodiment, if the stain type is not specified, then Automatic Stain Detection is used to determine the most likely stain type from the overall WSI image. In one embodiment of automatic stain detection, an SVM (Support Vector Machine) ML model is trained on color histogram data from a set of WSIs with known stain types, identified by an expert. The 2-dimensional color histogram used for model training characterizes the hue and saturation information for an entire WSI excluding the background areas. This process may require converting the WSI to both the desired resolution and the correct color space, such as the hue-saturation-value (HSV) color space, red-green-blue (RGB) color space, or a luminance-chrominance (e.g., YUV) color space. The pre-trained SVM then uses the histogram data to classify new WSIs with unknown staining types.

Preprocessing

Figure 2:
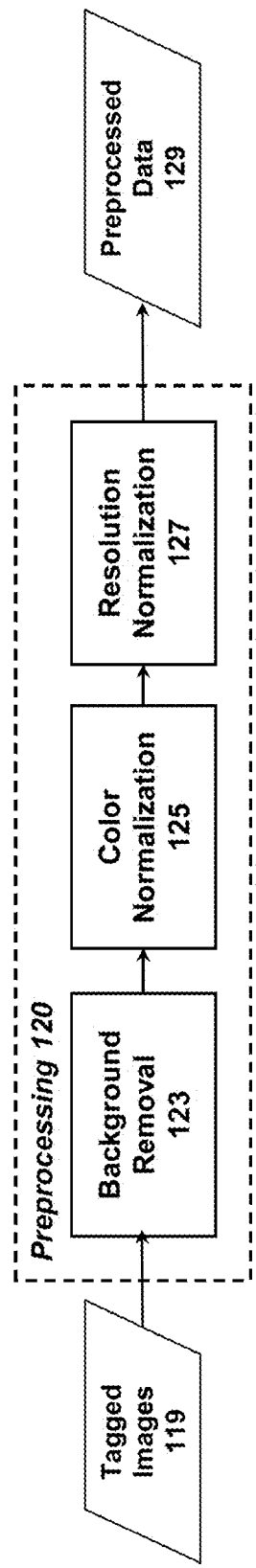
FIG. 2 illustrates an example system/method implementation of the Preprocessing Step in embodiments of the present invention.

Embodiments of the present invention perform preprocessing on images, such as in Step 120 of FIGS. 1 & 2. Preprocessing allows for images from multiple organizations to be aligned to a common format, resolution, or color profile for image processing and machine learning utilization. Individual organizations have their own protocols for processing a sample, including variations in stains, techniques, procedures, and WSI capture devices. In order to process these potentially disparate images through the same algorithms and processing pipeline, images may be normalized.

Normalization can take on many embodiments, but typically it may include color normalization (defining the optimal color characteristics for a given stain) and resolutional normalization (correcting discrepancies in Microns Per Pixel [mpp] between images).

Color normalization involves segmenting the WSI into foreground (tissue) and background, and applying a transform to make the foreground more closely conform to target stain colors and to whiten the background. The separation of foreground and background can be done in several ways. In one embodiment, such an algorithm detects the off-white or off-black background via value-based segmentation, by converting the image to grayscale and replacing large areas that are below, or above, a certain threshold (i.e., areas that are almost white or almost black) with an absolute white background. This step serves to remove any background artifacts. This brightness thresholding does not always work with darker and busy backgrounds. In another embodiment, segmentation is saturation-based. Foreground segmentation is based on the assumption that backgrounds are always less saturated in color than the tissue. Hence, the WSI is converted to hue-saturation-value color space, and then the saturation threshold is computed by finding a maximum of the second derivative of the saturation histogram. Then, the WSI is processed by comparing each pixel's saturation value to the threshold, creating the background/foreground mask.

Once the background is standardized, color deconvolution, or the classification and separation of the different stain components in the image by absorbance values, can be performed. In one embodiment, the classification of the components may be implemented using an SVM, k-nearest neighbors (KNN) algorithm, or some other similar ML classifier. In another embodiment, classification can be performed using matrix transformations on the absorbance values [Ruifrok & Johnston, "Quantification of histochemical staining by color deconvolution", *Anal Quant Cytol Histol,* 23: 291-299, 2001, http://ww.aqch.com/toc/auto_abstract.php?id=15581]. After the stain components of a WSI are separated, their color values in the given colorspace (e.g., RGB, HSV, etc.) are adjusted to match those of the deconvoluted target color components. The target colors may be determined by a professional, or by averaging the color components from training WSIs of known stain type.

Further embodiments may include at least one of spatial information and optical density information, in addition to chromatic information, to deconvolute the color components, in order to improve the accuracy of the normalization.

Resolution normalization is the processing of all input WSIs to identify or generate a resolution in microns per pixel (mpp) that is within a range of acceptable values based on what is required by the CNN. Some structures and features utilized by the CNN for its processing and classification are most visible at specific resolutions, so the normalization step ensures that all WSIs provide that data to the best degree possible.

In one embodiment, if a WSI contains multiple resolutions, and one of those resolutions falls within the range acceptable to the CNN, then that resolution is utilized for processing. If the acceptable range is of higher resolution than the maximum capture resolution, the highest capture resolution is scaled and smoothed using a scaling algorithm to produce the input data for the CNN. In a preferred embodiment, the scaling algorithm is bilinear interpolation. If the acceptable range falls between resolutions of the WSI, or is lower than the capture resolution, the next highest resolution in excess of the target resolution is selected, and the data is scaled and smoothed to produce the input data for the CNN.

Annotation

Figure 7:
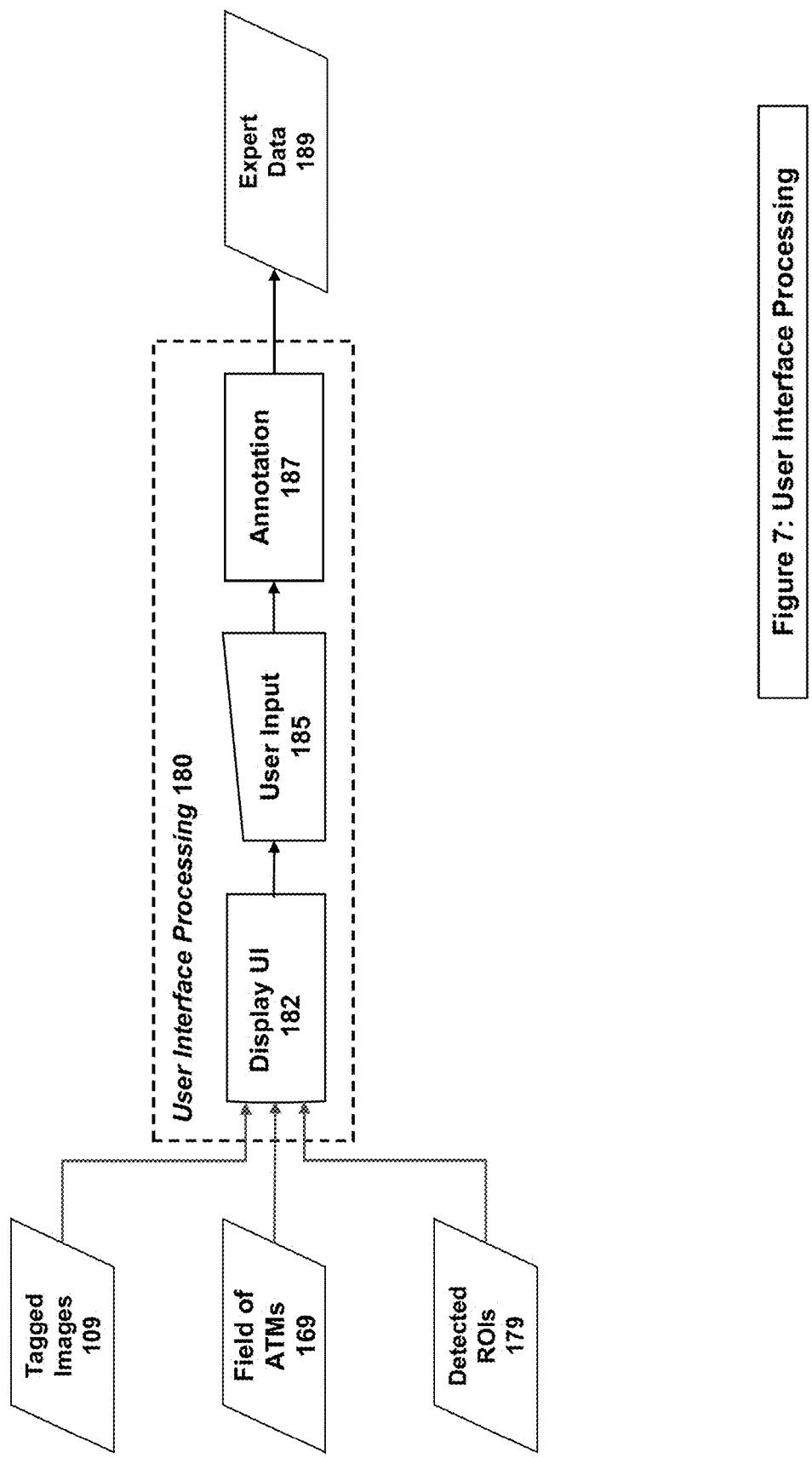
FIG. 7 illustrates an example system/method implementation of the User Interface Processing in embodiments of the present invention.
Figure 9:
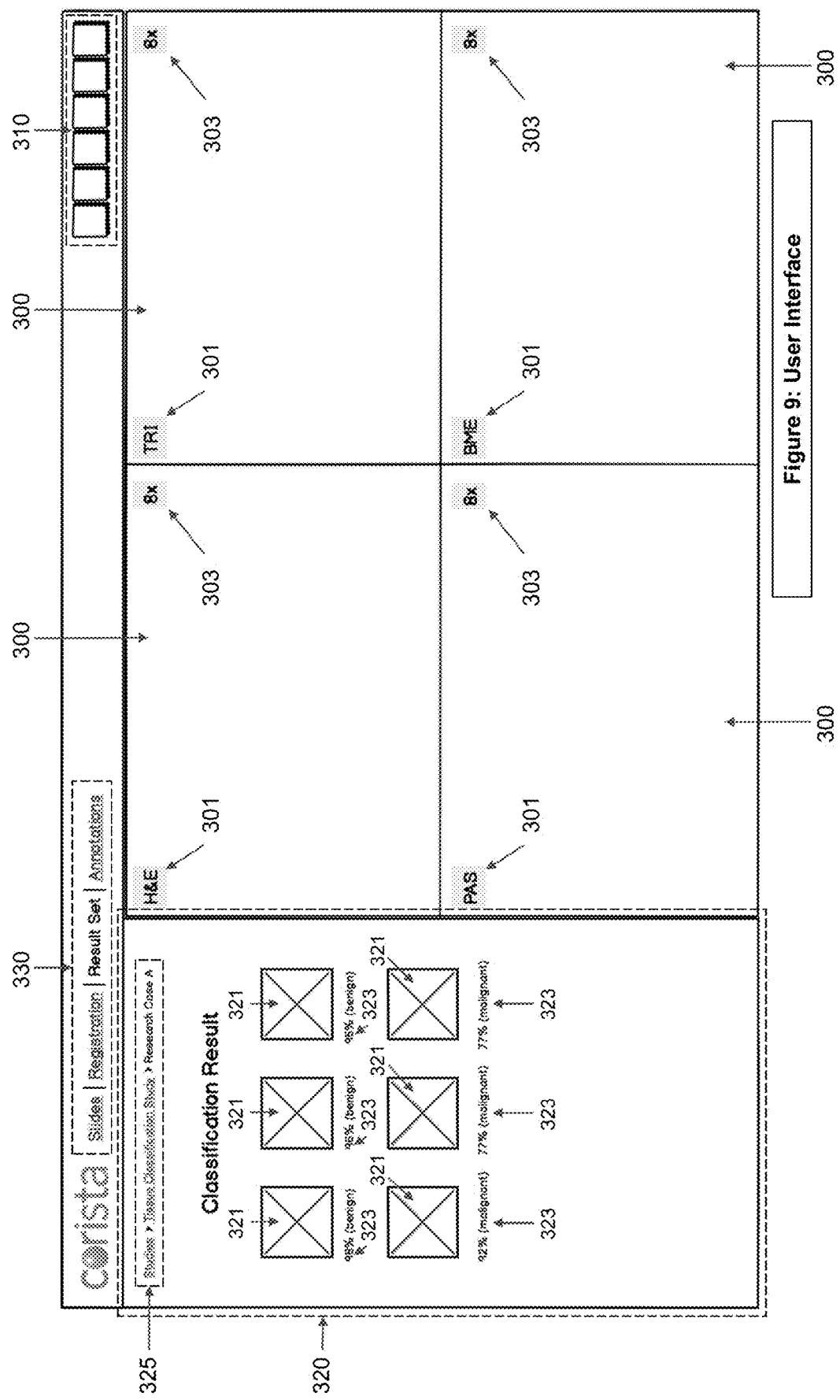
FIG. 9 illustrates a user interface for displaying classification results in embodiments of the present invention.

Embodiments of the present invention perform annotation on images, such as in Step 180 of FIGS. 1 & 7, using an interface such as the one specified in FIG. 9. Creation of a training set of data for Machine Learning (ML) algorithms can be accomplished in many ways. For the purpose of generating a training set, one or more annotations are specified, through an external system (i.e., importing annotations from a third-party), through an automated process (i.e., automated tissue segmentation algorithm), or by an expert user. The annotations may take one of two forms: WSI-based or region-based.

WSI-based annotations apply an annotation (i.e., label) to the entire image (minus the background, if applicable). Region-based annotations provide for the specification (by whichever process is used) of both one or more defined regions (such as an ellipse or polygon) of the WSI and the appropriate annotation for that region. In many embodiments, the assignment of a classification is a binary representation (a particular region either does or does not demonstrate a particular characteristic). In further embodiments, each region may also be assigned a class from a plurality of choices (such as normal, grade 1, grade 2, etc.).

In one example embodiment, an expert user may use annotations to define a region (e.g., an ellipse, a rectangular region, or a free-hand region) by highlighting the area that entirely contains a given feature for training a classifier. The annotated areas are then assigned a class based on the feature identified. Any subsections of the WSI containing tissue (not the background) which does not contain an expertly annotated classification are assigned a default classification, and can be used as such by the system during training.

In another embodiment, Computer Vision (CV) algorithms may be employed to facilitate the segmentation of the image (such as automated cell or nucleus detection, deconvolution, or color filtering). Once segmented, the expert can then more easily use one of the previously mentioned tools to mark a region as belonging to a specific class, and the expert may manually adjust the annotation to exclude those pieces not belonging to the class that fall within the region, or include those pieces belonging to the class that fall just outside of the region.

In another embodiment, the expert's annotations can be automatically classified into stricter categories such as "middle of the tissue" vs. "tissue borderline," which would allow for future training fine-tuning. This might be done by analyzing the color histogram of the annotated part of the WSI. For instance, finding significant background color peaks on the histogram would mean that annotation belongs to the "tissue borderline" category.

Creating an ML Model

Figure 4:
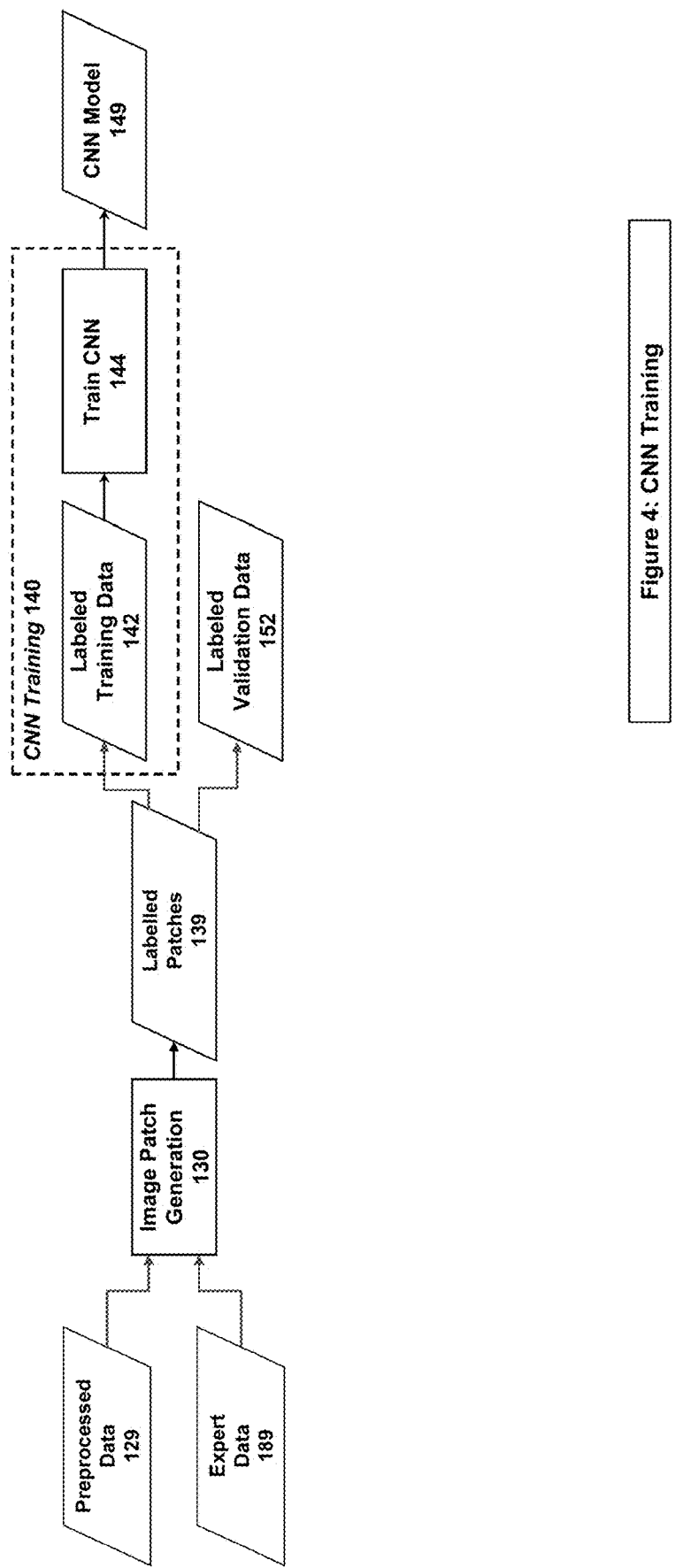
FIG. 4 illustrates an example system/method implementation of the CNN Training Step in embodiments of the present invention.
Figure 5:
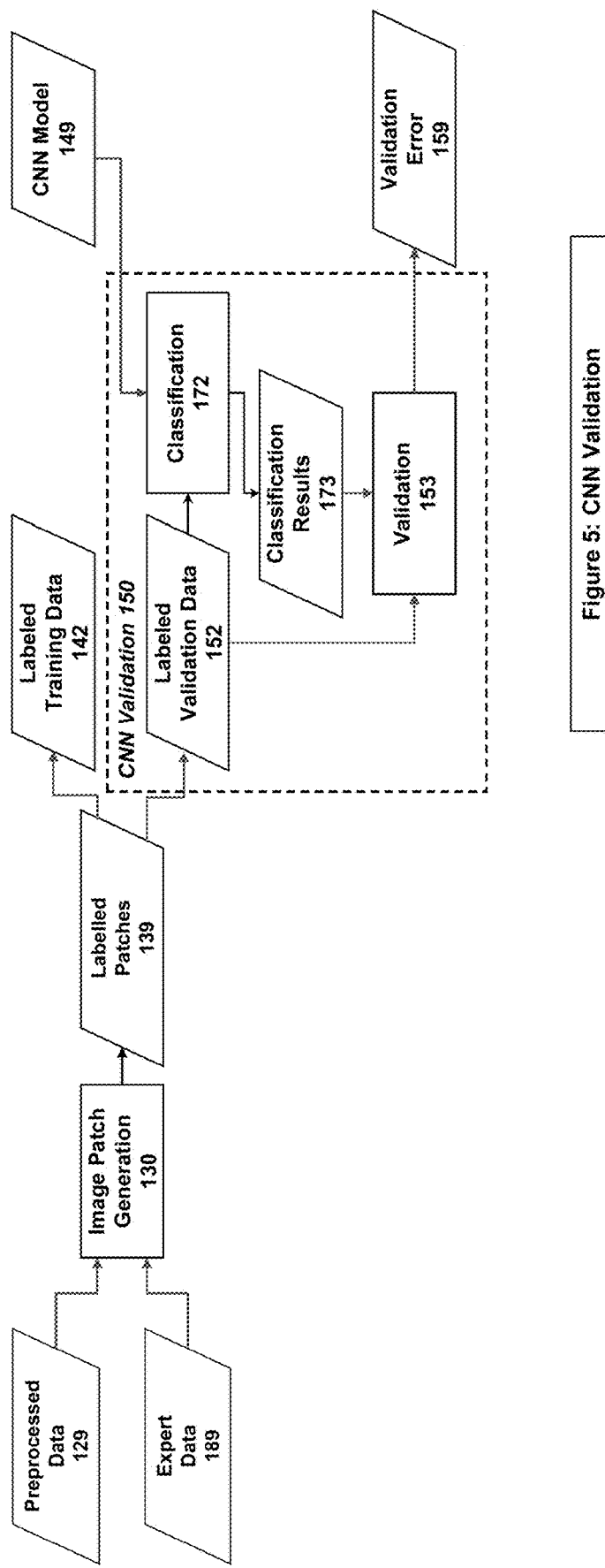
FIG. 5 illustrates an example system/method implementation of the CNN Validation Step in embodiments of the present invention.

Embodiments of the present invention create an ML model through training, such as in Step 140 of FIGS. 1 & 4. Once trained, the ML model can be validated to measure its performance on a validation data set, such as in Step 150 of FIGS. 1 & 5. Using the annotated images generated above, the next step is to train a model for future classification tasks. In some embodiments, from the annotated images, the system produces a series of image patches (smaller, overlapping segments of each image that can more readily be processed by the ML algorithm) and then assigns each patch a classification. For the more precisely annotated images, the specific regions of a particular class (as identified by the expert user) can be used as a mask to produce accurate training patches. Training patches can represent a subset of the normalized source image or may cover the entirety of the training image.

In an example embodiment, to further enrich and expand the set of training patches, the training patches can also be modified by rotation, flipping, scaling, adding noise, blurring, etc. to increase the overall size and variety of the dataset used for ML training. The set of annotated patches are then provided as training data to the ML algorithm, to produce the model. In another embodiment, the annotated images generated above could be divided into groups by certain criteria such as "middle of the tissue" vs "tissue borderline," with each group used to train a separate model.

In one embodiment, the model may be generated by training an ML algorithm, such as a Convolutional Neural Network (CNN) that operates on the raw image data. Other embodiments may include a preprocessing step before employing an ML algorithm, such as a Support Vector Machine (SVM) or a "shallow" Neural Network. In embodiments, preprocessing steps may include Image Processing (edge detection, sharpening, blurring, color manipulation/deconvolutions), Computer Vision, or Feature Detection (SURF, SIFT, BRISK, FREAK, ORB, etc.) algorithms.

In an example embodiment, the CNN may consist of two or more convolutional layers, pooling layers to reduce the dimensionality of the data and prevent overfitting, nonlinearity layers (e.g., Rectified Linear Unit [ReLU] layers) to increase the nonlinearity properties of the network, dropout layers to prevent overfitting, one or more fully-connected layers, and an output classification layer. In an embodiment, the classification layer is a softmax classifier with cross-entropy loss function. In one embodiment, the CNN's optimization algorithm for training is stochastic gradient descent with momentum (SGDM). In an alternate embodiment, the CNN's optimization algorithm is Adaptive Moment Estimation (ADAM).

CNNs differ from basic backpropagation neural networks (also known as multilayer perceptrons [MLPs]) in that CNNs are "deep" neural networks that contain more than one hidden layer (layers between the input and output layers). As such, CNNs dynamically generate features for classification (i.e., "on the fly") while training. This is distinguished from feature-based classifiers and classifiers that use basic backpropagation neural networks, which require a separate feature extraction step in which features useful for classification are explicitly calculated.

In an embodiment, the CNN may be trained from scratch using the WSI-based image patches generated as described above. In another embodiment, a CNN, which is pretrained on similar or dissimilar image data, may be imported via transfer learning, in which most of the layers of the pre-trained CNN are preserved and only the output classification layer is re-trained on the WSI image patch data.

In an embodiment, annotations (i.e., classifications or labels) are mapped to a set of desired output labels. During this process, the different annotations labels (either a pre-established set of human readable strings or numerical values) are mapped to the desired output labels. In one example, each different input label is mapped to an output label. In another example, all region-based annotations are mapped to a 'positive detection' and unannotated areas are deemed 'negative detections'. In a further example, a subset of input labels may be mapped to class A, another set to class B, and unannotated areas to class C.

In an example embodiment, more than one model may be trained, corresponding to particular capture characteristics (stain, lighting, imaging conditions, resolution) or specimen characteristics (e.g., shape, texture, etc.) or mapped output labels. In a further embodiment, preprocessing steps may be used to divide the training data by such characteristics into multiple sets of training data, such that separate models may be trained on different sets of training data, resulting in models that are "tuned" to and can more accurately classify image patches with those particular characteristics.

In one embodiment with multiple models, all of the models may be used simultaneously to inference a given WSI or area, utilizing a post-processing step, such as selecting the maximum confidence score from each model, to determine a final label based on the results from the individual models.

In a further embodiment with multiple models, a preprocessing step, leveraging Machine Learning models, Computer Vision processing or Feature Detectors, may be used to select the appropriate model from the multiple models for inferencing a particular region or for the WSI as a whole.

Once trained, the one or more ML models can be validated by subsequently testing the algorithm against samples of the labeled data to determine its validation error or training accuracy.

Evaluation of New Samples Against the Model (Classification)

Figure 6:
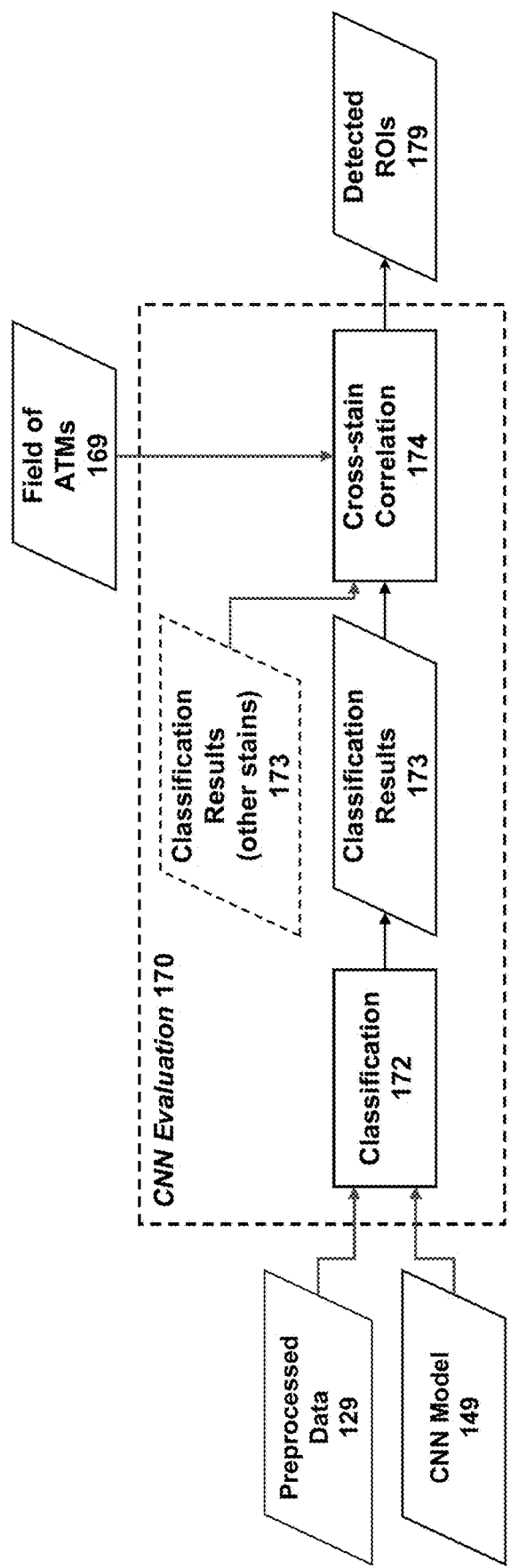
FIG. 6 illustrates an example system/method implementation of the Evaluation Step in embodiments of the present invention.

Embodiments of the present invention perform evaluation of new samples, such as in Step 170 of FIGS. 1 & 6. Classification is the evaluation of a new image (one not used for training) by a model. The classification step results in the assignment of a class with a confidence score based on the classes assigned during the training of the model. Without loss of generality, the classes may be referred to as "default" classifications, indicating the absence of the phenomenon of interest, and "non-default" classifications (or "detections"), indicating the presence of the phenomenon of interest. In example embodiments, non-default classifications may be further divided into sub-classes indicating different types of the phenomenon of interest.

In one embodiment, once the classification model has been computed on the training data for the CNN, it may be applied to "test" data to classify the test data. Similar to the training process, normalized and otherwise preconditioned image patches may be supplied to the model. The pipeline selected for the classifier accepts patches of a predetermined size as input and results in a classification and scoring of each patch based on the classes identified during training (either binary detection [default or non-default classifications] or n-class classifier [default classifications or non-default classifications with sub-classes]).

In another embodiment, the test data may be previously annotated and the results of the classification process may be compared to the test data annotations to determine how accurate the model is. In an embodiment, binary classification (i.e., detection) problems, in which a phenomenon (feature) may be declared present (positive or non-default classification) or absent (negative or default classification), may be evaluated via standard metrics such as sensitivity (correct positive percentage) or specificity (correct negative percentage) or F1 score.

In a further embodiment, incorrectly classified image patches may be collected and then fed back into the system to create a more accurate model via incremental training. The additional, incorrectly classified image patches may be added to the original training set to form a larger, combined training set. In one example embodiment, the CNN is re-trained from scratch on the combined training set. In another example embodiment, most of the layers of the original CNN are preserved, and the output classification layer is incrementally trained on the combined training set, via transfer learning. In an alternate embodiment, transfer learning is applied to the original CNN by retraining the output classification layer only on the "new" training data (the incorrectly classified image patches).

Registration

Figure 3:
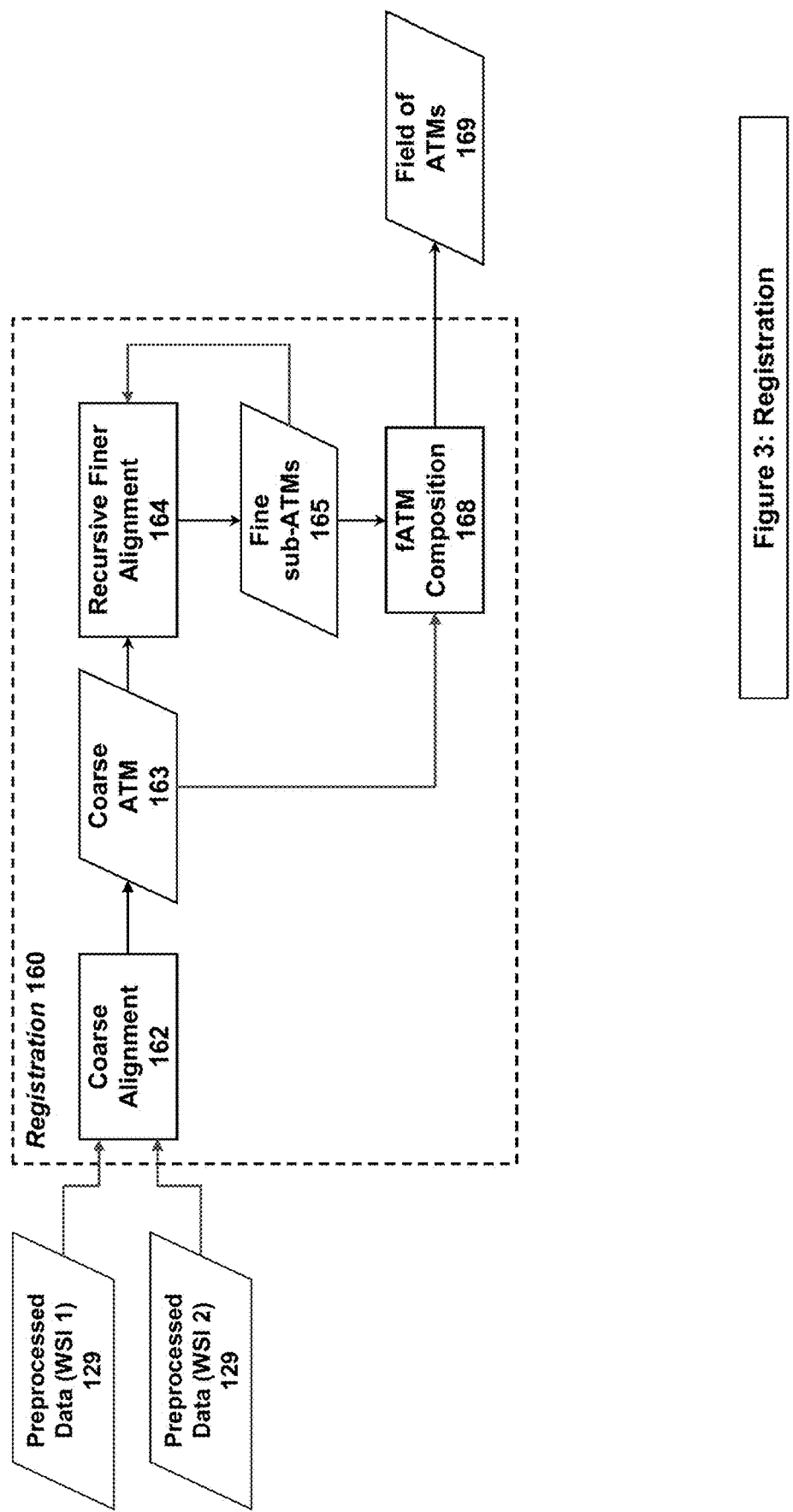
FIG. 3 illustrates an example system/method implementation of the Registration Step in embodiments of the present invention.

Embodiments of the present invention perform registration on the preprocessed WSIs, such as in Step 160 in FIGS. 1 & 3. The purpose of registering a pair of WSIs is to be able to translate any point on one registered WSI to a corresponding point on the other registered WSI. "Corresponding" in this context means belonging to the same (or nearly the same) physical location in the original 3D tissue sample. This is accomplished through the use of a spatially distributed set of affine transforms covering the entire WSI. The Affine Transform Matrices (ATMs) provide a simple mathematical way to correlate any point on the first image with a point on the second image.

At minimum, a single coarse ATM describing the alignment between whole images can be calculated. This is particularly useful to correlate highly irregular tissue in compared WSIs. A coarse ATM principally aligns the tissue to account for offsets (horizontal and vertical placement of the tissue on the slide), rotation (clockwise or counterclockwise rotation of the tissue, +/− 180 degrees), and inversion (where one specimen was flipped as it was placed on the slide).

The generation of an ATM can be achieved via identifying at least 3 matching keypoint pairs and then solving a linear system of equations using identified keypoint pairs. Keypoints are distinct positions in an image, usually relying on the visible features in the WSI such as tissue corners or blots. In each keypoint pair, one keypoint belongs to the first WSI and the second keypoint refers to the matching location on the second WSI. For example, the keypoint on a cellular feature in the first stained image (such as the edge of the tissue, or a cluster of red blood cells) should correspond to the same cellular feature in the second image. For the real world WSIs, there are usually more than three matching keypoint pairs identified, hence special mathematical methods are used to find the ATM that best satisfies all keypoint matches.

Normally, these keypoints are identified using a feature detection algorithm. In one embodiment, the ORB (Oriented FAST and rotated BRIEF) algorithm is used to detect keypoints, which are typically corners or edges in the image. The keypoints may be matched using a matching algorithm with an evaluation criterion. In one embodiment, this algorithm is the Brute-Force Matcher and the evaluation distance is the Hamming Distance, which is a measure of the differences between two strings. Next, the keypoint matches are analyzed for consistency, then unfit or poorly correlated matches are removed. The ATM candidates for the remaining matches may be found, further filtered for consistency, and then averaged to obtain a single, refined ATM for the region.

The process of averaging and finding the most correlated matches is done via an averaging algorithm. In one embodiment, the averaging algorithm is the Mean Shift clustering algorithm applied iteratively with dynamically configured parameters to achieve correlation goals. This clustering algorithm is executed several times with varying cluster size parameters, in order to find a cluster of correlated keypoints which is big enough to characterize most of the keypoint matches and at the same time compact enough to eliminate erroneous matching keypoints.

Using the information from the coarse ATM about the general translation and rotation of the WSIs, progressively finer ATMs can be calculated for smaller subsections of the images to improve precision, such that the WSI is divided by a "grid" of areas, each with a separate ATM. Fine ATMs provide better alignment precision than the coarse ATM, but they are only valid within a smaller subsection of the whole image. Finer ATMs are found because the images being registered are of biological origin and the physical tissue involved is cut, stained, and set by technicians; thus, there can be a variety of discrepancies among the images that would be difficult for an entire coarse WSI ATM to capture while maintaining good precision. There may be dislocations, folds, and other processing artifacts present on the images. Additionally, since the tissue sections are 2-dimensional slices of a 3-dimensional tissue, there can be differences in size, orientation, and presence of some of the features. With the small tissue subsections compared between the WSIs, the likelihood of the good match between them increases, hence enhancing the match precision.

In a preferred embodiment, a multi-resolution registration algorithm is used to provide fine ATMs at different stages. The image can be recursively divided into additional subsections of smaller size, generating progressively finer ATMs for each subsection based on the previously calculated ATMs, until no additional precision can be calculated, or the largest amount of subdivision is achieved. Once determined, these local ATMs comprise a progressively more precise, sparse pyramid of ATM levels, where higher precision fine ATMs represent smaller subsections of the images.

For some areas of the WSI, it is possible that they do not contain any detectable features (e.g., white background, missing portions of tissue). For these areas, the keypoints cannot be found, hence the ATM cannot be calculated. In one embodiment, for such feature-less subsections of the WSI, the local ATMs are computed by approximation from the previously computed nearby ATMs. In another embodiment, the ATM for these areas is taken from the lower precision ATM calculated for the bigger area, or from the entire coarse WSI ATM.

The combination of the most precise ATM for any region into a single structure creates a field of ATMs (fATMs).

In one embodiment for creating fATMs, a coarse ATM is initially generated using a low-resolution image that represents the whole image but is subsampled by many factors such as in step 162 FIG. 3. Once the coarse ATM is generated, the region of that ATM is broken into sub-regions, and a fine ATM is computed for each sub-region within the coarse ATM as in step 164 FIG. 3. The fine ATM for a region is evaluated based on evaluation criteria to determine if it is of sufficient quality to replace the coarse ATM for that region. If it is determined to be more precise based on the evaluation criteria, the fine ATM is inserted into the fATMs and can then be used as the basis for generation of finer ATMs for sub-regions of that region as in step 168 FIG. 3.

In another embodiment for creating fATMs, the coarser ATMs are calculated via a keypoint-based method as a first step to provide basic alignment of the two WSIs, and then a parametric, intensity-based registration algorithm is applied to bolster the coarse registration's precision. This algorithm compares the pixels of the two images instead of finding keypoints, matching up comparable areas based on a defined similarity metric and assessing the differences in the images in an iterative stochastic optimization process. This algorithm requires initial placement of the compared areas to be fairly good, hence the requirement of the keypoint WSI registration as a first step.

The keypoints-based registration and the intensity-based registration both may repeat on progressively smaller areas of WSIs, with higher resolution, as needed to obtain the optimal registration. Measuring the registration quality can be done in several ways. In one embodiment of the evaluation criteria, keypoints-based registration may be evaluated by the standard deviation and number of keypoints detected. For intensity-based registration, the second image is warped to fit the first image in the registration, producing a new result image. This result image can be overlayed on the first image to assess the quality of the registration, where greater non-overlapping area suggests a lower quality registration.

Correlation (Post-Processing)

Embodiments of the present invention perform correlation on classification results, such as in Step 172 of FIG. 6. In an embodiment, the outputs from the various classifiers may be combined and evaluated using a multitude of correlation techniques. The outputs from multiple input sets and multiple models may also be combined to boost the detection of the features and reduce false detections.

The output of the Correlation step is a set of ROIs, each of which may have a classification and an associated confidence metric (or score).

In one embodiment of such correlation, classification and scoring results may be obtained separately from several (e.g., four) stains of tissue WSIs. The per-staining detected feature results may be thresholded by a confidence score and combined together using inter-WSI registration in order to align the feature locations. The results may be further filtered out by removing spatial locations with positive detections on fewer than the required number of stain WSIs. The remaining positive classification data and scores may be merged into a score-heatmap, from which local combined score maxima are found, which in turn become the centers of newly found ROIs. Classification data may be further used after additional filtering to aggregate around the found local maxima and create clusters that would define the sizes of the newly found ROIs.

Using the combined classification results from possibly multiple stained WSIs and/or classification models with enhanced registration of WSI pairs utilized to correlate the localities of the positively classified areas results in significant improvement of the detection characteristics compared to the case of using a single image.

Display of Results & Feedback Loop

Embodiments of the present invention display results of the above steps to the user, such as in Step 180 of FIGS. 1 & 7, using an interface such as the one specified in FIG. 9. A basic example of this user interface display is presented in FIG. 9; number references in this section will refer to FIG. 9. In an embodiment, the user is presented with a software application for reviewing the WSIs and results of the CNN evaluation algorithm. The tool consists of a series of viewports (300) and a sidebar (320). The viewports each display a view of a differently stained, registered WSI (that is, the viewports display the similar location on each WSI). The sidebar can provide various tools, but during the review of results, the sidebar presents a series of thumbnails (321) representing the detected and classified ROIs. Each result may also contain further details (beyond location) as metadata (e.g., score, classification) (323). The results may also be visibly presented to the user as an annotation overlayed on the slides themselves. In one embodiment, the results may be colored or labeled differently based on result properties such as classification score, ML algorithm with the strongest classification, or classification category (i.e., output label) in the case of n-class classification. Furthermore, for n-class classifications, each individual class may be separately controlled as to whether it is viewable by the user, so that the user may visualize a single output classification, all output classifications or any combination desired.

In an example embodiment, the result thumbnails, when clicked, may navigate the corresponding viewport to the location indicated by the selected thumbnail. In the case of registered Multi-Sample WSIs, the interface may also navigate each viewport to the same or similar location on the corresponding stained slide based on the best available ATM generated by WSI registration. Clicking on any of the slide viewers, when panned or zoomed, triggers all other slide viewers to navigate to the same position by applying the best available ATM generated by registration. This ensures the same section of tissue across all WSIs is simultaneously viewable by the user.

In the preferred embodiment, if a user disagrees with the classification of a result generated by a model, the user can correct the classification by clicking a button next to the result thumbnail (e.g., false positive, incorrect classification). The corrected classification and result sub-image may then be used as future training data to improve the model. A user may also additionally annotate and classify regions of the slide which belong to a classification of the model that were not identified by the model. The corrected results and added classifications can then be used by the system to improve the model via retraining.

Digital Processing Environment

Figure 10:
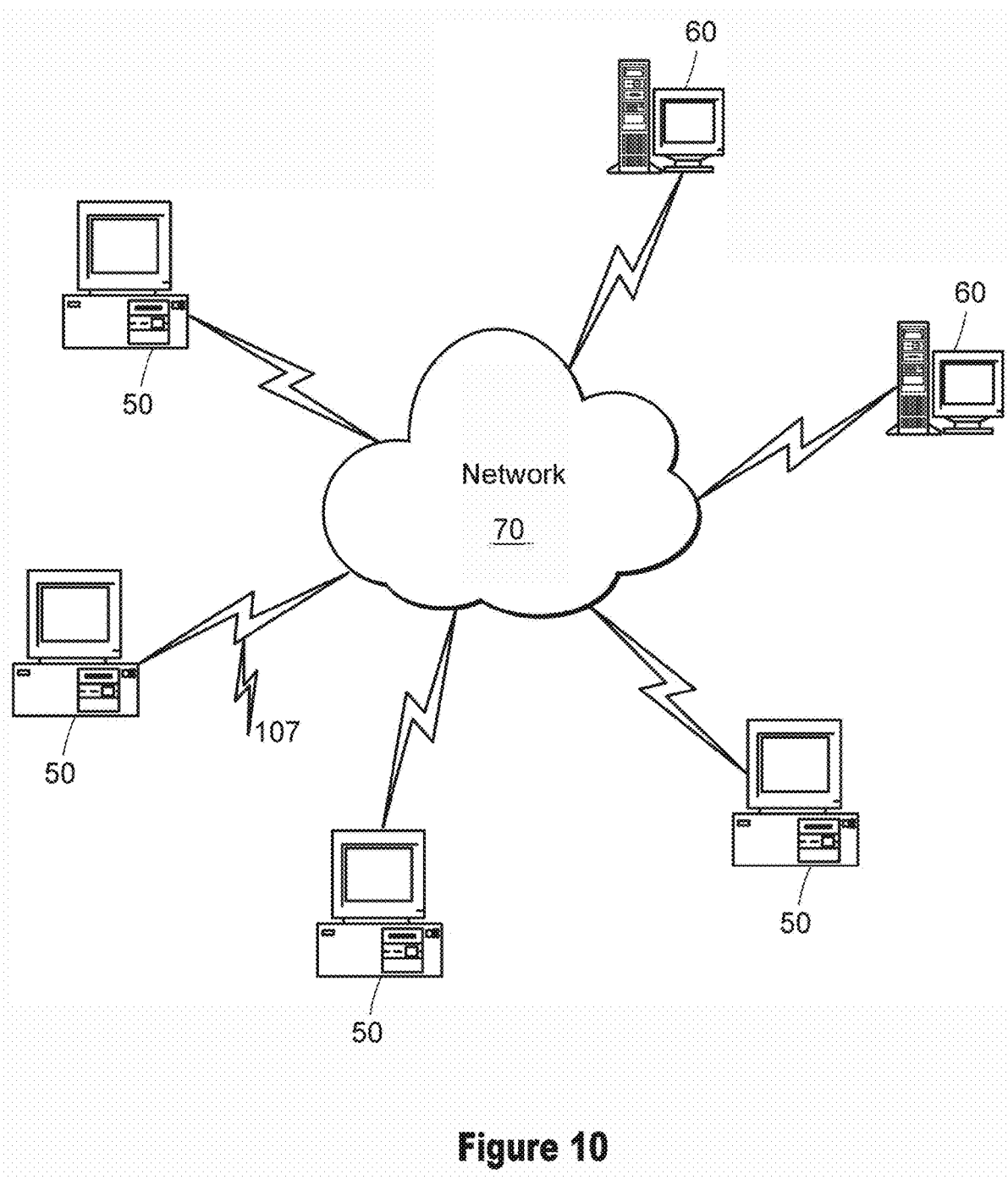
FIG. 10 illustrates an example digital processing environment in which embodiments of the present invention may be implemented.

FIG. 10 illustrates an example implementation of a WSI processing system according to an embodiment of the invention. The WSI processing system, which enables review of multiple WSIs, may be implemented in a software, firmware, or hardware environment. FIG. 10 illustrates one such example digital processing environment in which embodiments of the present invention may be implemented. Client computers/devices 50 and server computers/devices 60 (or a cloud network 70) provide processing, storage, and input/output devices executing application programs and the like. In other embodiments, client computer/devices 50 are locally connected (e.g., via a USB connection) across physical bounds to a processor on the server computers/devices 60 for communicating input to the server computers/devices 60.

Client computer(s)/devices 50 can also be linked through communications network 70 (e.g., via interface 107) to other computing devices, including other client devices/processes 50 and server computer(s) 60. Communications network 70 can be part of a remote access network, a global network (e.g., the Internet), cloud computing servers or service, a worldwide collection of computers, Local area or Wide area networks, and gateways that currently use respective protocols (TCP/IP, Bluetooth, etc.) to communicate with one another. Other electronic device/computer network architectures are suitable.

Client computers/devices 50 may include features to input WSI data (e.g., set of images for a specimen containing progressively different structures based on both sample variation and on the stains and light sources). The Client computer/devices 50 may also present a user interface tool consisting of a series of viewports to each display a view of differently stained registered WSI and a sidebar that may provide various tools and present a series of thumbnails representing detected and classified ROIs. Server computers 60 may be a user computer device, which may receive the input WSI data from the client computer/devices 50 and perform stain detection and image tagging on the WSI data. The server computers 60 may then perform on the tagged images preprocessing (color and resolution normalized), CNN training, evaluation for desired features, alignment (registered) across stains, post-processing (correlated), and displayed to a user via the user interface tool, as shown in FIGS. 1-9. The server computers may not be separate server computers but part of cloud network.

Figure 11:
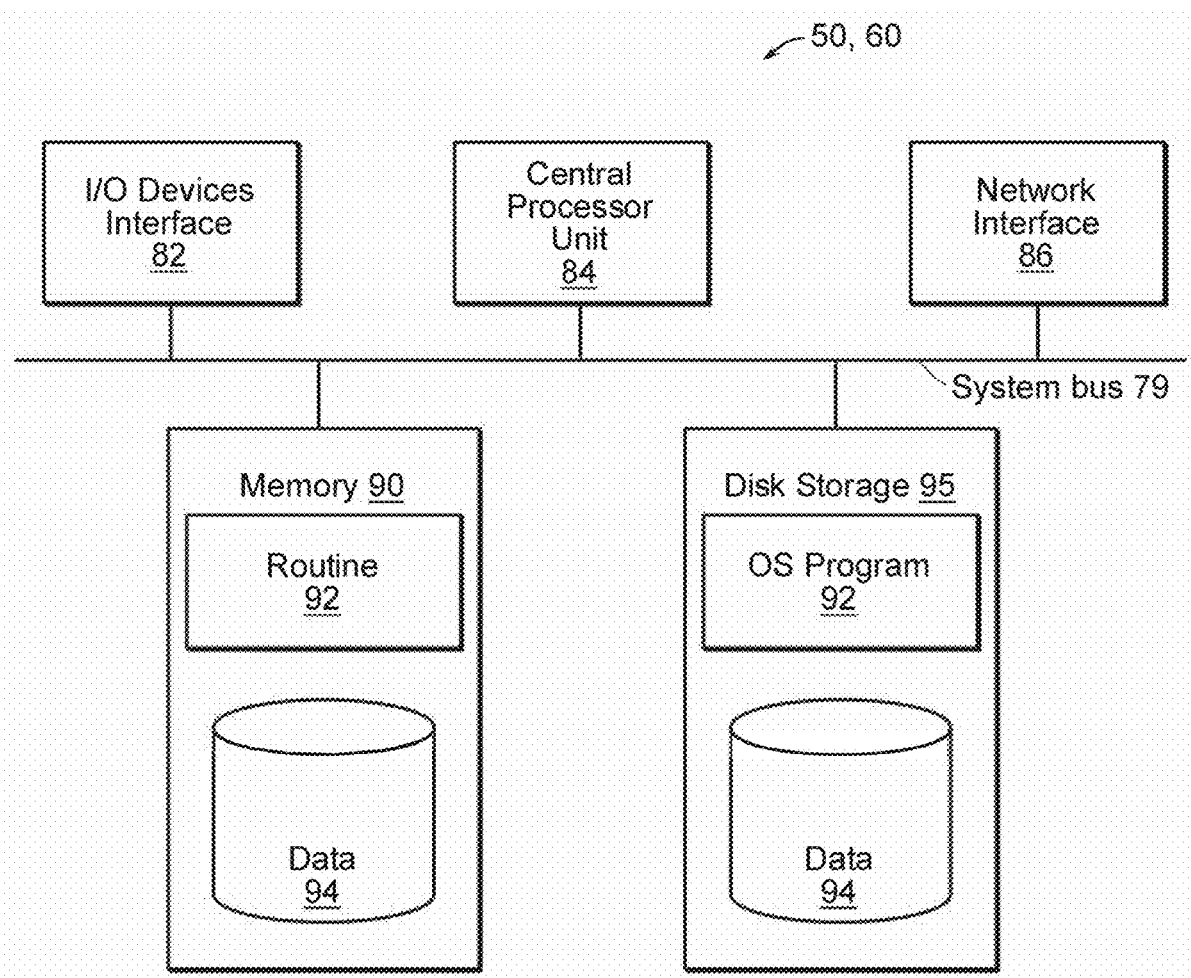
FIG. 11 illustrates a block diagram of the internal structure of a computer/computing node of FIG. 10.

FIG. 11 is a block diagram of the internal structure of a computer/computing node (e.g., client processor/device 50 or server computers 60) in the processing environment of FIG. 10, which may be used to facilitate processing audio, image, video or data signal information. Each computer 50, 60 in FIG. 11 contains system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements.

Attached to system bus 79 is I/O device interface 82 for connecting various input and output devices (e.g., keyboard, mouse, wheels, buttons, touch screens, displays, printers, speakers, voice controls, etc.) to the computer 50, 60. Network interface 86 allows the computer to connect to various other devices attached to a network (e.g., network 70 of FIG. 10), such as sensors, cameras, lasers, magnetometers. Memory 90 provides volatile storage for computer software instructions 92 and data 94 used to implement an embodiment of the present invention (e.g., code detailed above). Software components 92, 94 of the WSI processing system described herein may be configured using any programming language, including any high-level, object-oriented programming language.

In an example mobile implementation, a mobile agent implementation of the invention may be provided. A client-server environment can be used to enable mobile configuration of the capturing of the navigation of slide images. It can use, for example, the XMPP protocol to tether WSI data. The server 60 can then issue commands via the mobile phone on request. The mobile user interface framework to access certain components of the WSI processing system may be based on XHP, Javelin and WURFL. In another example mobile implementation for OS X, iOS, and Android operating systems and their respective APIs, Cocoa and Cocoa Touch may be used to implement the client side components 115 using Objective-C or any other high-level programming language that adds Smalltalk-style messaging to the C programming language.

Disk storage 95 provides non-volatile storage for computer software instructions 92 and data 94 used to implement an embodiment of the slide navigation system. The system may include disk storage accessible to the server computer 60. The server computer (e.g., user computing device) or client computer (e.g., sensors) may store information, such as images and models, from the reviewing of images. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the WSI processing system. Executing instances of respective software components of the WSI processing system, may be implemented as computer program products 92, and can be installed by any suitable software installation procedure, as is well known in the art. In another embodiment, at least a portion of the software instructions may also be downloaded over a cable, communication and/or wireless connection, via for example, a browser SSL session or through an app (whether executed from a mobile or other computing device). In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the routines/program 92 of the slide navigation system.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

In other embodiments, the program product 92 may be implemented as a so-called Software as a Service (SaaS), or other installation or communication supporting end-users.

While example embodiments have been particularly shown and described, it will be understood by those skilled in the art that various changes in form and details may be made therein without departing from the scope of the embodiments encompassed by the appended claims.

It should be noted that although the figures described herein illustrate example data/execution paths and components, one skilled in the art would understand that the operation, arrangement, and flow of data to/from those respective components can vary depending on the implementation and type of medical image data being processed. Therefore, any arrangement of data modules/data paths can be used.

While this invention has been particularly shown and described with references to example embodiments thereof, it will be understood by those skilled in the art that various changes in form and details may be made therein without departing from the scope of the invention encompassed by the appended claims.

In one example implementation, a blockchain system may be used to facilitate recording the registrations of the pre-processed WSIs from the stain sets of the multi-resolution registration algorithm. Annotations involves applying non-default classification labels to regions of the WSI data may, for example, further be recorded in a data blocks of a blockchain implementation. In this way, the registrations and annotations of the preprocessed WSIs may be recorded in a blockchain distributed ledger, which can facilitate maintaining the data integrity. Further, smart contracts can be used to control access to each WSI, and facilitate access among potentially disparate users.

What is claimed is:

1. A system for analyzing whole slide images (WSIs) of tissue specimens, the system comprising:
   at least one processor communicatively coupled to memory, where the at least one processor configured to:
   for each whole slide image (WSI) in a set of slides with a plurality of stains:
      specify a stain type for a whole slide image (WSI), where the stain type is specified through one of: metadata from another system, manual labeling by a pathologist or other domain expert, or an automatic stain detector;

preprocess the whole slide image (WSI) to separate the foreground tissue from the background and normalize the whole slide image (WSI) data based on parameters of a machine learning model, where the parameters include possible stains as well as resolution or other parameters;

present data of the whole slide image (WSI) for annotation, where the annotation involves applying non-default classification labels to regions of the whole slide image (WSI) data via a user interface by a pathologist or other domain expert;

create image patches from the annotated regions, each image patch corresponding to a single class;

train a parameter appropriate machine learning model that dynamically generates features useful for classification;

apply the trained machine learning model classifier to unannotated whole slide image (WSI) data to produce a set of classifications for the stain and patch parameters;

register the preprocessed whole slide images (WSIs) from the stain sets via a multi-resolution registration algorithm, the multi-resolution registration algorithm comprising: (1) an application of a coarse registration algorithm to produce a general Affine Transform Matrix and (2) iterative registration on successively smaller subsections to produce a sparse hierarchical multi-resolution Affine Transform Matrix pyramid, which is then processed to generate a non-sparse Field of Affine Transform Matrices (fATMs) such that corresponding regions between images are aligned to the highest degree possible based on tissue and imaging variations;

aggregate the non-default classification labels from multiple stain sets, each set of classifications generated by applying a stain-specific, trained machine learning model to the normalized whole slide image (WSI) data, with the aggregation achieved through the translation of the non-default classifications using the fATMs generated for the individual whole slide images (WSIs); and correlate the aggregated non-default classifications from each of the multiple whole slide images (WSIs) in the stain set, then correlating the individual classifications by enhancing true classifications and removing false classifications, resulting in one or more non-default classified regions for a given stain set and metadata for the one or more non-default classified regions of the given stain set.

2. The system as in claim 1, wherein algorithms for the machine learning are implemented by Deep Learning or Convolutional Neural Networks (CNNs), Region-based CNNs (R-CNN), Support Vector Machines (SVMs), Auto-Encoders (AEs) or Shallow Neural Networks (SNNs).

3. The system as in claim 2, wherein output from Convolutional Neural Network (CNN) are post-processed by applying at least one algorithm including thresholding of confidence scores, combining detections using interstain registration, filtering, and creation of score heat-maps.

4. The system as in claim 1, wherein the input whole slide images (WSIs) are separated or classified, with regards to stain, using a machine learning algorithm, SVM, based on color profile, color histogram or other differentiating features.

5. The system as in claim 1, wherein the background is removed from the whole slide image (WSI) and corresponding patches as a pre-processing step, differentiating foreground and background using one or more of value-based or saturation-based comparison.

6. The system as in claim 1, wherein the annotations are imported into the system and transformed into the appropriate format for use by the machine learning model, for training or evaluation of the model, instead of being created by an expert annotator within the system.

7. The system as in claim 1, wherein the annotations are either imported or specified by an expert annotator, and the annotation label is whole slide image (WSI)-based, where all labels are applied to the entire whole slide image (WSI), and, consequently, all of the tissue on the whole slide image (WSI), or region-based, where one or multiple annotated sections, including the specification of the region and the labels, are applied in order to differentiate specific features on the whole slide image (WSI).

8. The system, as in claim 1, where the whole slide image (WSI) can be preprocessed, using an algorithm, to segment, pre-annotate or annotate the image, for the purposes of augmenting an expert annotator's annotations or as the annotation source for training.

9. The system as in claim 1, where a cohort of patches or regions from a whole slide image (WSI), which are intended for training a Convolutional Neural Network (CNN) are augmented using at least one processing technique including scaling, rotation, flipping, addition of noise, blurring, stretching, or skewing to increase the overall size and variety of the dataset used for training.

10. The system as in claim 1, wherein a Convolutional Neural Network (CNN) is pretrained on a set of image data external to the system and imported into the system via transfer learning, in which most of the layers of the pre-trained Convolutional Neural Network (CNN) are preserved and only the output classification layer is re-trained on the system's whole slide image (WSI) image patch data.

11. The system as in claim 1, wherein the annotation labels provided as an input to the training process for a model are preprocessed to map the plurality of inputs to a user-specified set of output labels, where one or more input labels are mapped to a single output label.

12. The system as in claim 1, wherein more than one Convolutional Neural Network (CNN) model are trained, each model corresponding to particular data characteristics, resulting in models tuned to image patches with those particular characteristics, resulting in a more accurate classification of the image patches using the more than one Convolutional Neural Network (CNN) model;

wherein the cohort of models are used for inferencing on new whole slide images (WSIs) and the resulting scores are then evaluated through post-processing to determine a final classification.

13. The system as in claim 1, wherein more than one Convolutional Neural Network (CNN) model are trained, each model corresponding to particular data characteristics, resulting in models tuned to image patches with those particular characteristics, resulting in a more accurate classification of the image patches using the more than one Convolutional Neural Network (CNN) model;

wherein preprocessing is used to determine which model to use for inferencing for the entire whole slide image (WSI) or on a region-by-region basis, with a final result being returned via inferencing by the selected model.

14. The system as in claim 1, wherein selected regions of the whole slide image (WSI) identified as incorrectly classified image patches are collected and fed back into the system to create a more accurate model via incremental training, by adding the incorrectly classified image patches to the original training set to form a larger, combined training set or by retraining on a set of data favoring the corrected image patches.

15. The system as in claim 1, wherein the coarse or fine registration algorithms are specified, by the user or by a system process, from at least one of: keypoint matching, ORB (Oriented FAST and rotated BRIEF) features or intensity-based matching.

16. The system as in claim 15, wherein progressively higher-resolution (increased detail) registration is calculated by dividing an existing registered region into subsections, and processing registration algorithms on the subsections;
   wherein a supersection's registration is comprised of a multitude of the subsections, the supersection's registration being used as an initial guide for the progressively higher-resolution (increased detail) registration.

* * * * *